US00PP08462P

United States Patent [19]

VandenBerg

[11] Patent Number: Plant 8,462

[45] Date of Patent: Nov. 16, 1993

[54] CHRYSANTHEMUM PLANT NAMED RUMBA

[75] Inventor: Cornelis P. VandenBerg, Salinas, Calif.

[73] Assignee: Yoder Brothers, Inc., Barberton, Ohio

[21] Appl. No.: 936,250

[22] Filed: Aug. 27, 1992

[51] Int. Cl.[5] ..... A01H 5/00

[52] U.S. Cl. ..... Plt./76

[58] Field of Search ..... Plt./76, 80, 81, 82.4, Plt./74.1

[56] References Cited

U.S. PATENT DOCUMENTS

P.P. 2,023 2/1961 Dunham ..... Plt. 76

*Primary Examiner*—Howard J. Locker

*Attorney, Agent, or Firm*—Foley & Lardner

[57] ABSTRACT

A Chrysanthemum plant named Rumba particularly characterized by its flat capitulum form; pompon capitulum type; pink ray floret color; diameter across face of capitulum of 38 to 48 mm when fully opened, when grown as a single stem spray cut mum; photoperiodic flowering response to short days of 55 to 56 days when grown in Salinas, Calif., and of 65 to 68 days when grown in Bogota, Colombia; plant height of 79 to 81 cm with 11 long days after planting rooted cuttings prior to start of short days when grown as a single stem cut mum, with no growth regulator applications when grown in Salinas; when grown in Bogota with 14 to 15 long days prior to start of short days plant height is 102 to 114 cm; peduncle length at flowering time of the first lateral after removing the apical bud when grown in Salinas is 8 to 10 cm; peduncle length of the fourth lateral is 13 to 15 cm; when grown in Bogota, peduncle length of the first and fourth lateral is 13 to 20 cm and 20 to 23 cm, respectively; and excellent tolerance to low night temperatures for bud initiation and flower development.

3 Drawing Sheets

The present invention comprises a new and distinct cultivar of Chrysanthemum, botanically known as *Dendranthema grandiflora,* referred to by the cultivar name Rumba.

Rumba, identified as 1925 (89-942008), was originated from a cross made by Cornelis P. VandenBerg in a controlled breeding program in Salinas, Calif., in 1988.

The female parent of Rumba was an unnamed seedling identified as 0481 (85-891006), and described as a spray cut mum with a small pompon capitulum type; a light pink ray floret color; diameter of capitulum of 44 mm to 51 mm; a flowering response to short days of 56 to 69 days under normal conditions in Salinas, Calif.; a plant height of 91 to 104 cm with 7 to 14 long days after planting rooted cuttings prior to start of short days; peduncle length of the first lateral after removing the apical bud of 13 to 18 cm, when grown in Salinas. The female parent was discarded in Apr. 1991.

The male parent of Rumba was an unnamed seedling, identified as 1514 (85-276010) and described as a cut spray mum with a small decorative to pompon capitulum type with many disc florets; a medium pink ray floret color; diameter of capitulum of 38 to 44 mm; a flowering response to short days of 51 to 61 days under normal conditions in Salinas, Calif.; a plant height of 81 to 104 cm with 6 to 14 long days after planting rooted cuttings prior to start of short days; peduncle length of the first lateral after removing the apical bud of 10 to 13 cm, and peduncle length of the fourth lateral of 13 to 18 cm when grown in Salinas. The male parent was discarded in Apr. 1988.

Rumba was discovered and selected as one flowering plant within the progeny of the stated cross by Cornelis P. VandenBerg in Jan. 1990, in a controlled environment in Salinas, Calif.

The first act of asexual reproduction of Rumba was accomplished when vegetative cuttings were taken from the initial selection in Apr. 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Rumba are firmly fixed and are retained through successive generations of asexual reproduction.

Rumba has not been observed under all possible environmental conditions. The phenotype may vary significantly with variations in environment such as temperature, light intensity and daylength, without, however, any variation in genotype.

The following observations, measurements and comparisons describe plants grown in Salinas, Calif. and in Bogata, Colombia under greenhouse conditoins which approximate those generally used in commercial greenhouse practice.

The following traits have been repeatedly observed and are determined to be basic characteristics of Rumba, which, in combination, distinguish this Chrysanthemum as a new and distinct cultivar:

1. Flat capitulum form.
2. Pompon capitulum type.
3. Pink ray floret color.
4. Diameter across face of capitulum of 38 to 48 mm when fully opened, when grown as a single stem spray cut mum.
5. Photoperiodic flowering response to short days of 55 to 56 days when grown in Salinas, Calif., and of 65 to 68 days when grown in Bogota, Colombia.
6. Plant height of 79 to 81 cm with 11 to 14 long days after planting rooted cuttings prior to start of short days when grown as a single stem cut mum, with no growth regulator applications when grown in Salinas. When grown in Bogota with 14 to 15 long days prior to start of short days plant height is 102 to 114 cm.

7. Peduncle length at flowering time of the first lateral after removing the apical bud when grown in Salinas is 8 to 10 cm; peduncle length of the fourth lateral is 13 to 15 cm; when grown in Bogota, peduncle length of the first and fourth lateral is 13 to 20 cm and 20 to 23 cm, respectively.

8. Excellent tolerance to night temperatures as low as 5°-10° C. for bud initiation and flower development.

The accompanying photographic drawings show typical inflorescence and leaf characteristics of Rumba, with the colors being as nearly true as possible with illustrations of this type.

Sheet 1 is a color photograph of a side view of Rumba grown as a single stem cut mm.

Sheet 2 is a black and white photograph of three views of the inflorescence of Rumba.

Sheet 3 is a black and white photograph showing the upper and under sides of the leaves of Rumba at 3 stages of development (mature, intermediate and immature). In sheets 2 and 3 a measuring tape in centimeters has been added.

No commercial cultivar known to the inventor is similar in comparison to Rumba. The combination of the pompon capitulum type, pink ray floret color, and excellent low night temperature tolorance for bud initiation and flower development is unique, and is not represented in any cultivar known to the inventor.

In the following description color references are made to The Royal Horticultural Society Colour Chart. The color values were determined on plant material grown as a single stem spray cut mum in Salinas, Calif. on Mar. 26, 1992.

Classification:

*Botanical.*—*Dendranthema grandiflora* cv Rumba.

*Commercial.*—Pompon spray cut mum.

INFLORESCENCE

A. Capitulum:

*Form.*—Flat.

*Type.*—Pompon.

*Diameter across face.*—38 to 48 mm when fully opened.

B. Corolla of ray florets:

*Color (general tonality form a distance of three meters).*—Pink.

*Color (upper surface).*—78C to 78 D.

*Color (under surface).*—70A to 70C.

*Shape of petals.*—Straight, tubular to strongly concave spooned.

C. Corolla of disc florets:

*Color (mature).*—12A.

*Color (immature).*—Closest to 145B.

D. Reproductive organs:

*Androecium.*—Present on disc florets only; scant pollen.

*Gynoecium.*—Present on both ray and disc florets.

PLANT

A. General appearance:

*Height.*—79 to 81 cm when grown as a single stem spray cut mum with 11 long days after planting rooted cuttings prior to start of short days, with no growth regulator applications when grown in Salinas, Calif. When grown in Bogota, Colombia with 14 to 15 long days prior to start of short days, plant height ranges from 102 to 114 cm.

B. Foliage:

*Color (upper surface).*—147A.

*Color (under surface).*—147B.

*Shape.*—See photograph.

I claim:

1. A new and distinct Chrysanthemum plant named Rumba, as described and illustrated.

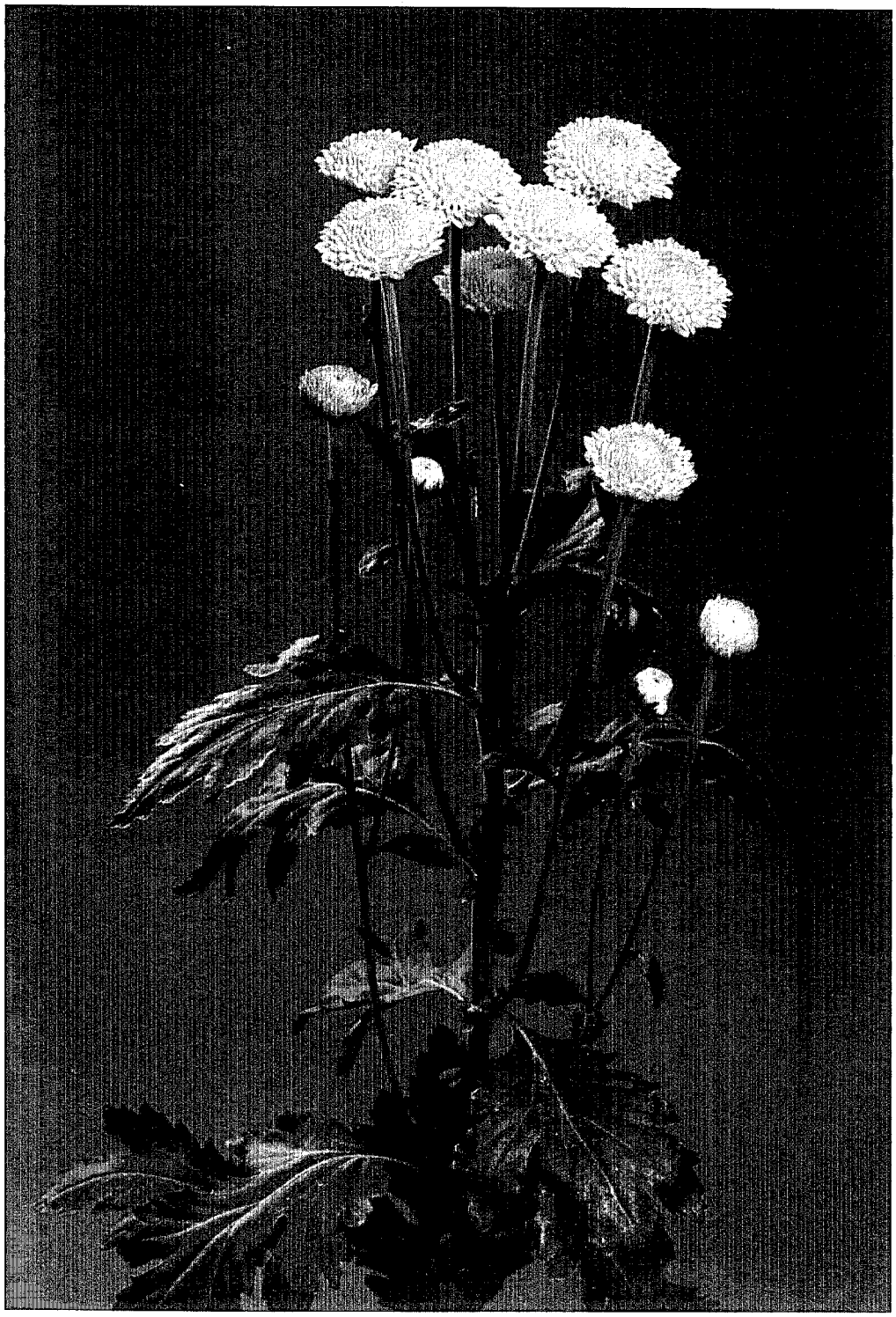

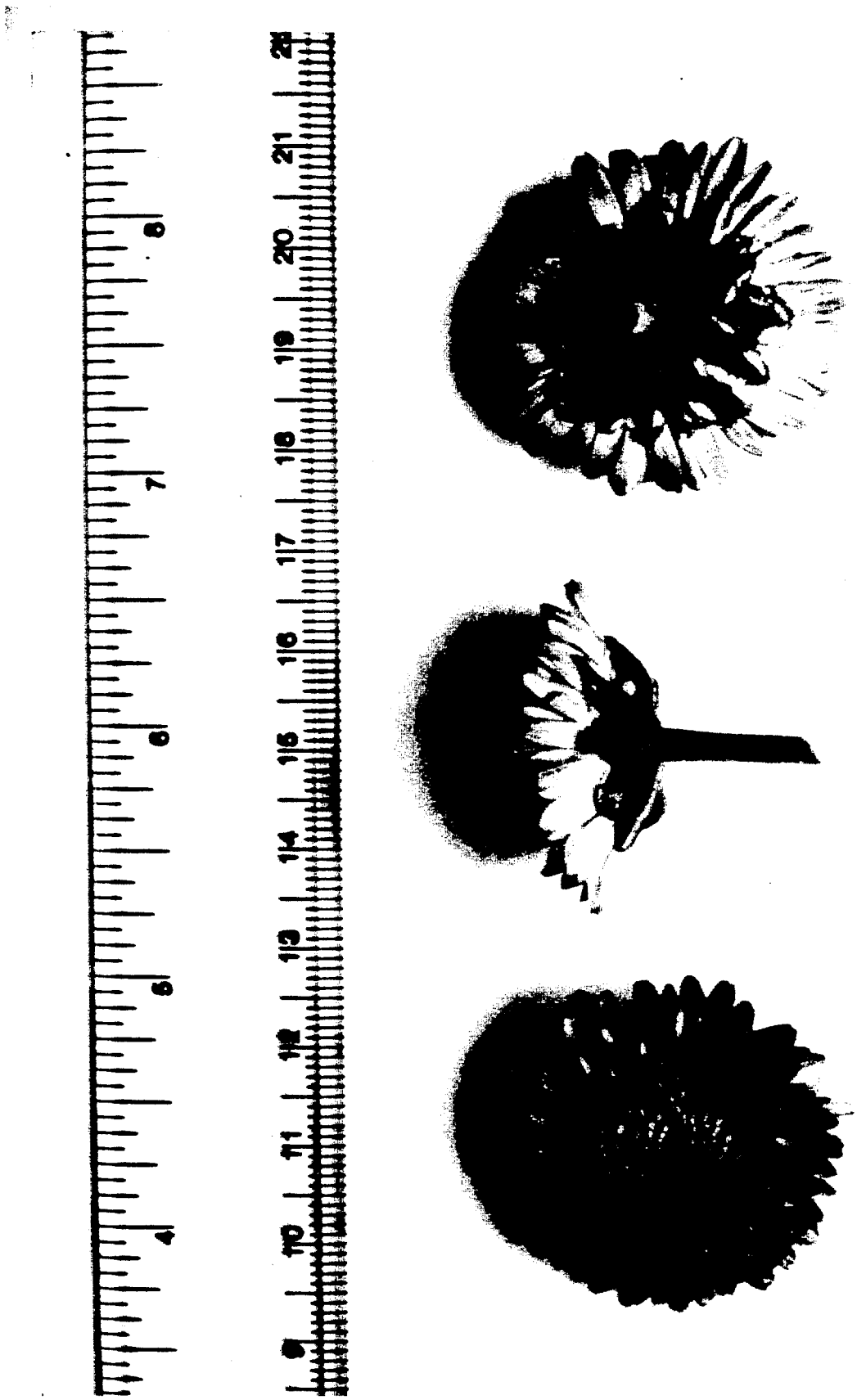

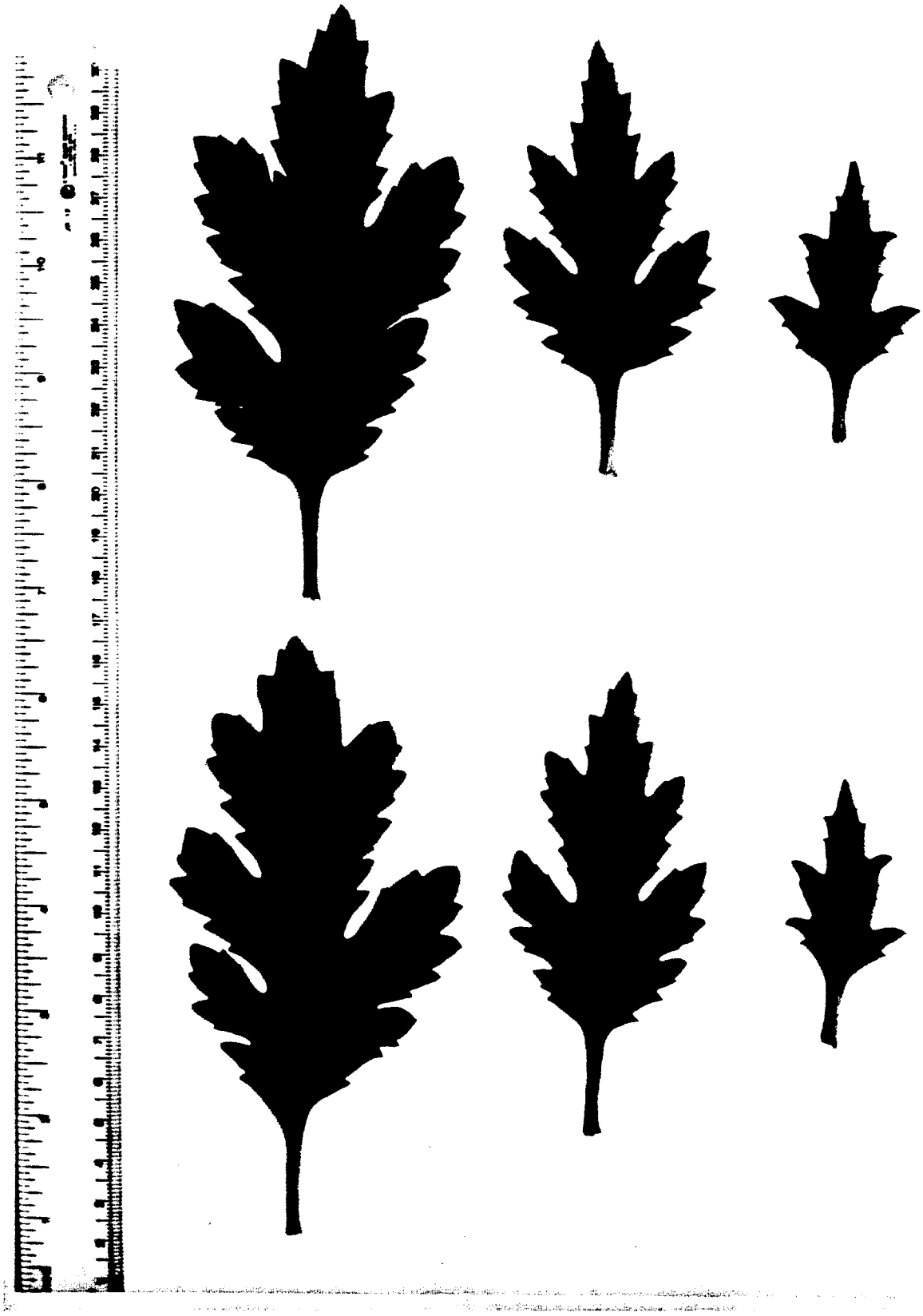

* * * * *